(12) United States Patent
Byron et al.

(10) Patent No.: US 10,518,004 B2
(45) Date of Patent: Dec. 31, 2019

(54) INFECTION FIGHTING DRUG ELUTING DEVICE

(71) Applicant: Cardiac Pacemakers, Inc., St. Paul, MN (US)

(72) Inventors: Mary M. Byron, Roseville, MN (US); David R. Wulfman, Minneapolis, MN (US); Angelo Fruci, Mahtomedi, MN (US); Adam McGraw, Manfield, MA (US); Danielle Frankson, Dayton, MN (US); Gregory J. Sherwood, North Oaks, MN (US); Joseph T. Delaney, Jr., Minneapolis, MN (US); Adeniyi O. Aremu, Brooklyn Park, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 0 days.

(21) Appl. No.: 15/843,673

(22) Filed: Dec. 15, 2017

(65) Prior Publication Data

US 2018/0169307 A1    Jun. 21, 2018

Related U.S. Application Data

(60) Provisional application No. 62/435,829, filed on Dec. 18, 2016.

(51) Int. Cl.
| | | |
|---|---|---|
| A61L 31/16 | (2006.01) | |
| A61L 31/14 | (2006.01) | |
| A61L 31/04 | (2006.01) | |
| A61N 1/05 | (2006.01) | |
| D01D 5/00 | (2006.01) | |

(52) U.S. Cl.
CPC .............. *A61L 31/16* (2013.01); *A61L 31/04* (2013.01); *A61L 31/148* (2013.01); *A61N 1/0568* (2013.01); *A61L 2300/404* (2013.01); *D01D 5/003* (2013.01); *D10B 2331/06* (2013.01); *D10B 2509/00* (2013.01)

(58) Field of Classification Search
None
See application file for complete search history.

(56) References Cited

U.S. PATENT DOCUMENTS

| | | | |
|---|---|---|---|
| 4,676,782 A | 6/1987 | Yamamoto et al. | |
| 5,154,182 A | 10/1992 | Moaddeb | |
| 5,217,493 A | 6/1993 | Raad et al. | |
| 5,861,023 A | 1/1999 | Vachon | |
| 6,267,782 B1 | 7/2001 | Ogle et al. | |
| 6,451,003 B1 | 9/2002 | Prosl et al. | |
| 7,067,606 B2 | 6/2006 | Mather et al. | |
| 7,174,221 B1 | 2/2007 | Chen et al. | |
| 7,322,965 B2 | 1/2008 | Gibson et al. | |
| 7,507,230 B2 | 3/2009 | Li et al. | |
| 7,947,301 B2 | 5/2011 | Bischoff et al. | |
| 8,209,016 B2 | 6/2012 | Deininger et al. | |
| 8,308,713 B2 | 11/2012 | Li et al. | |
| 8,430,852 B2 | 4/2013 | Bischoff et al. | |
| 8,628,798 B2 | 1/2014 | Halliday et al. | |
| 2007/0190880 A1* | 8/2007 | Dubrow ................. | B01D 39/08 442/181 |
| 2011/0201984 A1* | 8/2011 | Dubrow ................. | A61F 13/02 602/54 |
| 2015/0025608 A1 | 1/2015 | Delaney et al. | |
| 2015/0284587 A1* | 10/2015 | Schallenberger ........ | B05D 1/18 523/122 |
| 2016/0176107 A1 | 6/2016 | Wulfman et al. | |

FOREIGN PATENT DOCUMENTS

| | | |
|---|---|---|
| WO | WO9307924 A1 | 4/1993 |
| WO | 2005084582 A1 | 9/2005 |
| WO | 2007078304 A2 | 7/2007 |
| WO | WO2008134478 A2 | 11/2008 |

OTHER PUBLICATIONS

H1465. Implantable Lead Infection Barrier. Jul. 4, 1995. Stokes, et. al. 4 pages.
Huang, Zheng-Ming et al., "A review on polymer rianolibers by electrospinning and their applications in nanocomposites", Composites Science and Technology, No. 66, 2003, pp. 2223-2253.
International Search Report and Written Opinion issued in PCT/US2017/066690, dated Apr. 3, 2018, 14 pages.

\* cited by examiner

*Primary Examiner* — Jennifer A Berrios
(74) *Attorney, Agent, or Firm* — Faegre Baker Daniels LLP (57) ABSTRACT

An implantable drug eluting medical device includes a polymer substrate having a surface, a first plurality of nanofibers, and at least one antimicrobial drug. Each of the first plurality of nanofibers includes a first portion interpenetrated with the surface of the substrate to mechanically fix the nanofiber to the substrate, and a second portion projecting from the surface. The at least one antimicrobial drug is disposed within or among the second portion of the first plurality of nanofibers.

8 Claims, 7 Drawing Sheets

INFECTION FIGHTING DRUG ELUTING DEVICE

CROSS-REFERENCE TO RELATED APPLICATION

This application claims priority to Provisional Application No. 62/435,829, filed Dec. 18, 2016, which is herein incorporated by reference in its entirety.

TECHNICAL FIELD

The present invention relates to preventing infections associated with implantable medical devices. More specifically, the invention relates to an infection fighting drug eluting device for an implantable medical electrical lead.

BACKGROUND

Medical devices may be implanted in a subcutaneous pocket to support sensing intrinsic physiological electrical activity, delivering a therapeutic stimulus to patient tissue, or providing other therapy to specific treatment sites. For example, a pulse generator may be implanted in a subcutaneous pocket in a patient's chest, with one or more electrical leads extending from the pulse generator to treatment sites within the patient.

Implanting a medical device within a patient exposes the patient to a risk of a nosocomial (e.g., hospital-acquired) infection associated with bacteria adhering to the exterior of the medical device when it is placed within the subcutaneous pocket, causing a pocket infection. For example, the average nosocomial infection rate associated with the implantation of cardiovascular implantable electronic devices in 2008 was approximately 2.4 percent. In some cases of infection, the implantable medical device, including the device housing and any associated electrical leads, must be completely removed. Following removal, the infection must be cured and the patient must heal enough to tolerate implantation of a replacement medical device. The costs of such infections may be significant, not only intrinsically, but also in terms of the physical and emotional stress suffered by the patient.

What is needed is a way to reduce the occurrence of infections which may result from implanting a medical device within a patient.

SUMMARY

Example 1 is an implantable drug eluting medical device including a polymer substrate having a surface, a first plurality of nanofibers, and at least one antimicrobial drug. Each of the first plurality of nanofibers includes a first portion interpenetrated with the surface of the substrate to mechanically fix the nanofiber to the substrate, and a second portion projecting from the surface. The at least one antimicrobial drug is disposed within or among the second portion of the first plurality of nanofibers.

Example 2 is the implantable medical device of Example 1, wherein the first plurality of nanofibers is formed of a bioresorbable polymer and the at least one antimicrobial drug is disposed within the second portion of the first plurality of nanofibers.

Example 3 is the implantable medical device of Example 1, wherein the second portion of the first plurality of nanofibers forms a first plurality of pores and the at least one antimicrobial drug is disposed within at least some of the first plurality of pores among the second portion of the first plurality of nanofibers.

Example 4 is the implantable medical device of Example 3, further including cross-linked poly(ethylene glycol) containing the at least one antimicrobial drug, the cross-linked poly(ethylene glycol) containing the at least one antimicrobial drug disposed within the first plurality of pores and mechanically fixed to the second portion of the first plurality of nanofibers.

Example 5 is the implantable medical device of Example 4, wherein the cross-linked poly(ethylene glycol) containing the at least one antimicrobial drug is bonded to the second portion of the first plurality of nanofibers by covalent bonds.

Example 6 is the implantable medical device of any of Examples 1-5, further comprising a second plurality of nanofibers disposed on the first plurality of nanofibers, the second plurality of nanofibers forming a second plurality of pores.

Example 7 is the implantable medical device of Example 6, wherein the second plurality of nanofibers are thermally bonded to the first plurality of nanofibers.

Example 8 is the implantable medical device of either of Examples 6 or 7, wherein the second plurality of pores has an average pore size that is smaller than an average pore size of the first plurality of pores.

Example 9 is the implantable medical device of any of Examples 6-8, further comprising a second at least one antimicrobial drug disposed among the second plurality of nanofibers, wherein the second at least one antimicrobial drug can be the same or different than the at least one antimicrobial drug disposed within or among the second portion of the first plurality of nanofibers.

Example 10 is a method of forming a drug eluting layer on a surface of a polymer substrate of an implantable medical device. The method includes interpenetrating a first portion of a first plurality of nanofibers within the surface of the substrate while the surface of the substrate is in a liquid or semi-liquid state, solidifying the surface of the substrate such that the first portion of the first plurality of nanofibers is mechanically fixed within the surface of the substrate and a second portion of the first plurality of nanofibers projects away from the surface, and incorporating at least one antimicrobial drug within pores formed by the second portion of the first plurality of nanofibers.

Example 11 is the method of Example 10, wherein incorporating the at least one antimicrobial drug within pores formed by the second portion of the first plurality of nanofibers includes blending the at least one antimicrobial drug with a poly(ethylene glycol), disposing the blend of the at least one antimicrobial drug and the poly(ethylene glycol) into the pores, and cross-linking the poly(ethylene glycol) to mechanically fix the blend of the at least one antimicrobial drug and the poly(ethylene glycol) to the second portion of the first plurality of nanofibers.

Example 12 is the method of Example 11, further including exposing the second portion of the first plurality of nanofibers and the blend of the at least one antimicrobial drug and the poly(ethylene glycol) to an argon-containing plasma to covalently bond the cross-linked poly(ethylene glycol) to the second portion of the first plurality of nanofibers.

Example 13 is the method of any of Examples 10-12, wherein interpenetrating the first portion of the first plurality of nanofibers within the surface of the substrate includes electro-spinning the first plurality of nanofibers directly into the surface of the substrate.

Example 14 is the method of any of Examples 10-12, wherein interpenetrating the first portion of the first plurality of nanofibers within the surface of the substrate includes electro-spinning the first plurality of nanofibers onto a core pin or a mandrel, and over-molding the surface of the substrate onto the first portion of the first plurality of nanofibers on the core pin or mandrel.

Example 15 is the method of any of Examples 10-14, further comprising electro-spinning a second plurality of nanofibers onto the first plurality of nanofibers before incorporating at least one antimicrobial drug within pores formed by the second portion of the first plurality of nanofibers.

Example 16 is an implantable drug eluting medical device including a polymer substrate having a surface, a first plurality of nanofibers, and at least one antimicrobial drug. Each of the first plurality of nanofibers includes a first portion interpenetrated with the surface of the substrate to mechanically fix the nanofiber to the substrate, and a second portion projecting from the surface. The at least one antimicrobial drug is disposed within or among the second portion of the first plurality of nanofibers to elute from the device.

Example 17 is the implantable medical device of Example 16, wherein the first plurality of nanofibers is formed of a bioresorbable polymer and the at least one antimicrobial drug is disposed within the second portion of the first plurality of nanofibers.

Example 18 is the implantable medical device of either of Examples 16 or 17, wherein the second portion of the first plurality of nanofibers forms a first plurality of pores and the at least one antimicrobial drug is disposed within at least some of the first plurality of pores among the second portion of the first plurality of nanofibers.

Example 19 is the implantable medical device of Example 18, further including cross-linked poly(ethylene glycol) containing the at least one antimicrobial drug, the cross-linked poly(ethylene glycol) containing the at least one antimicrobial drug disposed within the first plurality of pores and mechanically fixed to the second portion of the first plurality of nanofibers.

Example 20 is the implantable medical device of Example 19, wherein the cross-linked poly(ethylene glycol) containing the at least one antimicrobial drug is bonded to the second portion of the first plurality of nanofibers by covalent bonds.

Example 21 is the implantable medical device of any of Examples 16-20, further comprising a second plurality of nanofibers disposed on the first plurality of nanofibers, the second plurality of nanofibers forming a second plurality of pores.

Example 22 is the implantable medical device of Example 21, wherein the second plurality of nanofibers are thermally bonded to the first plurality of nanofibers.

Example 23 is the implantable medical device of either of Examples 21 or 22, wherein the second plurality of pores has an average pore size that is smaller than an average pore size of the first plurality of pores.

Example 24 is the implantable medical device of any of Examples 21-23, further comprising a second at least one antimicrobial drug disposed among the second plurality of nanofibers, wherein the second at least one antimicrobial drug can be the same or different than the at least one antimicrobial drug disposed within or among the second portion of the first plurality of nanofibers.

Example 25 is the implantable medical device of any of Examples 16-24, wherein first plurality of nanofibers has an average diameter ranging from about 100 nanometers to about 1,000 nanometers.

Example 26 is a method of forming a drug eluting layer on a surface of a polymer substrate of an implantable medical device. The method includes interpenetrating a first portion of a first plurality of nanofibers within the surface of the polymer substrate of the device while the surface of the substrate is in a liquid or semi-liquid state, solidifying the surface of the substrate such that the first portion of the first plurality of nanofibers is mechanically fixed within the surface of the substrate and a second portion of the first plurality of nanofibers projects away from the surface of the substrate, and incorporating at least one antimicrobial drug within pores formed by the second portion of the first plurality of nanofibers.

Example 27 is the method of Example 26, wherein incorporating the at least one antimicrobial drug within the pores formed by the second portion of the first plurality of nanofibers includes blending the at least one antimicrobial drug with a poly(ethylene glycol), disposing the blend of the at least one antimicrobial drug and the poly(ethylene glycol) into the pores, and cross-linking the poly(ethylene glycol) to mechanically fix the blend of the at least one antimicrobial drug and the poly(ethylene glycol) to the second portion of the first plurality of nanofibers.

Example 28 is the method of Example 27, further including exposing the second portion of the first plurality of nanofibers and the blend of the at least one antimicrobial drug and the poly(ethylene glycol) to an argon-containing plasma to covalently bond the cross-linked poly(ethylene glycol) to the second portion of the first plurality of nanofibers.

Example 29 is the method of any of Examples 26-28, wherein interpenetrating the first portion of the first plurality of nanofibers within the surface of the substrate includes electro-spinning the first plurality of nanofibers directly into the surface of the substrate.

Example 30 is the method of any of Examples 26-28, wherein interpenetrating the first portion of the first plurality of nanofibers within the surface of the substrate includes electro-spinning the first plurality of nanofibers onto a core pin or a mandrel, and over-molding the surface of the substrate onto the first portion of the first plurality of nanofibers on the core pin or mandrel.

Example 31 is the method of any of Examples 26-30, further comprising electro-spinning a second plurality of nanofibers onto the first plurality of nanofibers before incorporating at least one antimicrobial drug within pores formed by the second portion of the first plurality of nanofibers.

Example 32 is the method of any of Examples 26-31, wherein solidifying the surface of the substrate includes cross-linking the polymer substrate around the first portion of the first plurality of nanofibers.

Example 33 is a method of forming a drug eluting layer on a surface of a polymer substrate of an implantable medical device. The method includes blending at least one antimicrobial drug with a bioresorbable polymer, electro-spinning the blend of the at least one antimicrobial drug and the bioresorbable polymer to form a plurality of nanofibers, interpenetrating a first portion of the plurality of nanofibers within a surface of the substrate while the surface of the substrate being in a liquid or semi-liquid state, and solidifying the surface of the substrate such that the first portion of the plurality of nanofibers is mechanically fixed within the surface of the substrate and a second portion of the plurality of nanofibers projects away from the surface of the substrate.

Example 34 is the method of Example 33, wherein interpenetrating the first portion of the plurality of nanofibers within the surface of the substrate includes electrospinning the plurality of nanofibers directly into the surface of the substrate.

Example 35 is the method of Example 33, wherein interpenetrating the first portion of the plurality of nanofibers within the surface of the substrate includes electrospinning the plurality of nanofibers onto a core pin or a mandrel, and over-molding the surface of the substrate onto the first portion of the plurality of nanofibers on the core pin or mandrel.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention. The detailed description of the invention which follows is intended to illustrate but not limit the invention.

In accordance with various aspects of the disclosure, it is understood that the various embodiments can be implemented in any suitable medical device implanted in a patient that includes an electrical lead electrically connected to the housing, such as the cardiac rhythm management (CRM) system described below. For example, embodiments may be employed with a subcutaneously-implanted implantable cardioverter-defibrillator (ICD) housing and lead system. Other such implantable medical devices include, without limitation, implantable cardiac monitors and neurostimulation systems such as spinal cord stimulation or deep brain stimulation devices.

Figure 1:
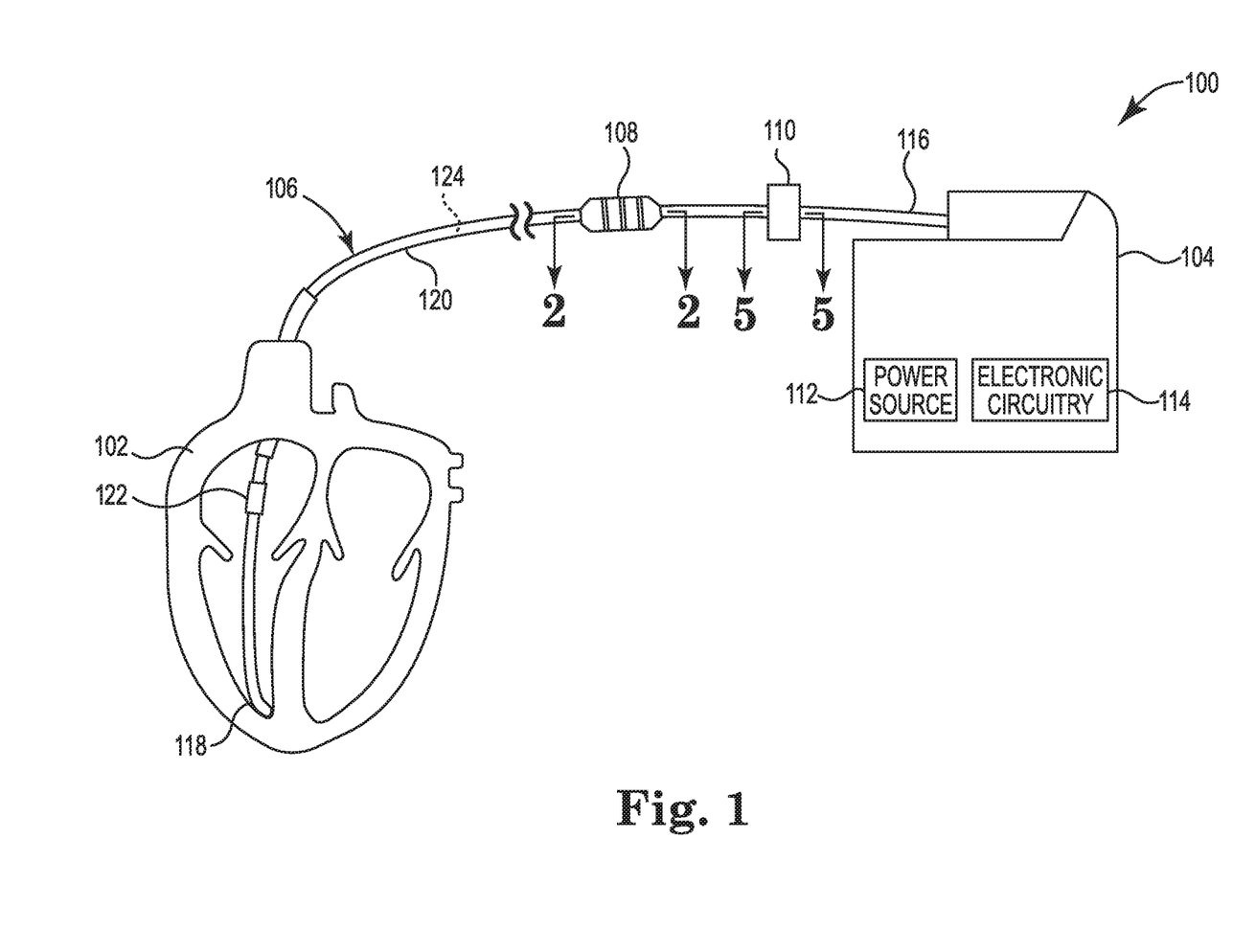
FIG. 1 is a schematic illustration of implantable medical devices in accordance with some embodiments of the disclosure.

FIG. 1 is a schematic illustration of implantable medical devices in accordance with some embodiments of the disclosure. FIG. 1 shows a cardiac rhythm management (CRM) system 100 for delivering and/or receiving electrical pulses or signals to stimulate, shock, and/or sense a heart 102. The CRM system 100 can include a pulse generator 104, a medical electrical lead 106, a suture sleeve 108, and a ring 110. The pulse generator 104 includes a power source 112 as well as electronic circuitry 114. The power source 112 may be a battery. The electronic circuitry 114 may be configured to generate a series of timed electrical discharges or pulses. The pulse generator 104 may be implanted into a subcutaneous pocket made in the wall of the chest. Alternatively, the pulse generator 104 may be placed in a subcutaneous pocket made in the abdomen, or in another location. It should be noted that while the medical electrical lead 106 is illustrated for use with a heart 102, the medical electrical lead 106 is suitable for other forms of electrical stimulation/sensing as well.

In some embodiments, the medical electrical lead 106 extends from a proximal end 116, where it is coupled with the pulse generator 104, to a distal end 118, which is coupled with a portion of the heart 102, when implanted or otherwise coupled therewith. The medical electrical lead 106 includes a lead body 120 extending generally from the proximal end 116 to the distal end 118. The lead body 120 may be a tubular structure. Disposed along a portion of the medical electrical lead 106, for example near the distal end 118, may be at least one electrode 122 which electrically couples the medical electrical lead 106 with the heart 102. At least one electrical conductor 124 (shown in FIG. 2) may be disposed within the lead body 120 and extend generally from the proximal end 116 to the distal end 118. The at least one electrical conductor 124 electrically connects the electrode 122 with the proximal end 116 of the medical electrical lead 106 to couple the electrode 122 to the pulse generator 104. The electrical conductor 124 carries electrical current and pulses between the pulse generator 104 and the electrode 122, and to and from the heart 102.

The medical electrical lead 106 can be secured in place by the suture sleeve 108 as described below in reference to FIG. 2. Migration and dislodgment of the medical electrical lead 106 may be discouraged by securing the suture sleeve 108 about the lead body 120 and suturing the suture sleeve 108 to the patient's tissue. The suture sleeve 108 can be an implantable drug eluting device, according to embodiments of the disclosure.

Additionally or alternatively, the ring 110 can also be a drug eluting device, according to embodiments of the disclosure. The ring 110 fits around the lead body 120 and may be disposed anywhere along the length of the lead body 120.

The ring 110 can be an implantable drug eluting device, according to embodiments of the disclosure.

Embodiments according to the disclosure, such as the suture sleeve 108 and the ring 110, may elute at least one antimicrobial drug. The eluting antimicrobial drug can weaken or kill bacteria adhering to the surface of the suture sleeve 108 or the ring 110 as a result of, for example, the suture sleeve 108 or ring 110 being set down on operating spaces and/or being moved around during implantation of the CRM system 100. Once the CRM system 100 is implanted, a sufficient dosage of the at least one antimicrobial drug can elute from the suture sleeve 108 within the subcutaneous pocket and/or the ring 110 in the subcutaneous pocket or the venous pathway to reduce incidence and/or severity of a pocket infection or endocarditis.

In some embodiments, the at least one antimicrobial drug can include a broad-spectrum antibiotic, such as minocycline; or a narrow-spectrum antibiotic, such as rifampin. A broad-spectrum antibiotic is an antimicrobial drug that acts against a wide range of disease-causing bacteria, e.g. against both Gram-positive and Gram-negative bacteria. A narrow-spectrum antibiotic is an antimicrobial drug that acts against a single family of bacteria, e.g. Gram-positive or Gram-negative, but not both. In some embodiments, the at least one antimicrobial drug can include a combination of a broad-spectrum antibiotic and a narrow-spectrum antibiotic, such as a combination of minocycline and rifampin. In some embodiments, the at least one antimicrobial drug can include daptomycin, sulfonamide drugs, β-lactams, and/or vancomycin.

Although the embodiment shown in FIG. 1 is illustrated with one suture sleeve 108 and one ring 110, it is understood that embodiments may include only one of either the suture sleeve 108 or the ring 110. Embodiments may also include more than one suture sleeve 108 and/or more than one ring 110. For example, more rings 110 may be added to increase the dosage of the at least one antimicrobial drug delivered to the subcutaneous pocket.

Figure 2:
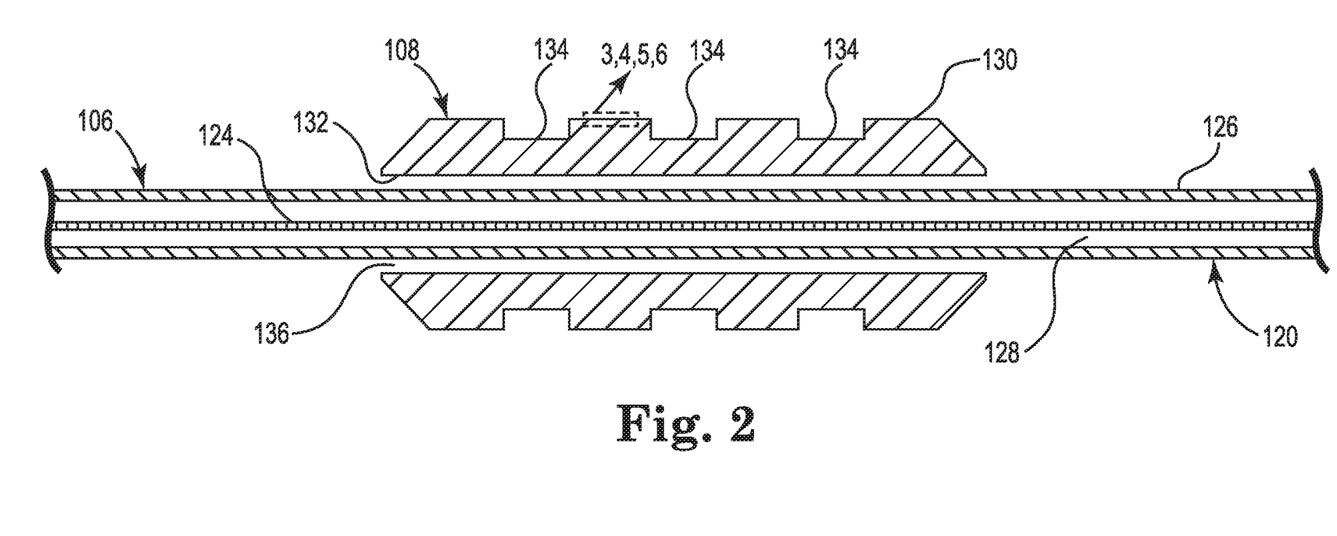
FIG. 2 is a schematic cross-sectional view of a portion of the implantable medical electrical lead of FIG. 1 showing a suture sleeve about the lead body.

FIG. 2 is a schematic cross-sectional view of a portion of the implantable medical electrical lead 106 of FIG. 1 showing the suture sleeve 108 about the lead body 120. In the embodiment shown in FIG. 2, the lead body 120 includes a tubular structure 126 defining a lead lumen 128. The electrical conductor 124 extends through the lead lumen 128 from the proximal end 116 to the electrode 122 (FIG. 1). The suture sleeve 108 includes an outer surface 130 and an inner surface 132. In the embodiment of FIG. 2, the suture sleeve 108 also includes at least one suture groove 134 (three shown) in the outer surface 130 extending around the circumference of the suture sleeve 108. The inner surface 132 defines a suture sleeve lumen 136 extending the length of the suture sleeve 108. A diameter of the suture sleeve lumen 136 is greater than a diameter of the lead body 120 such that the suture sleeve lumen 136 may be moved along the lead body 120 to a position adjacent to tissue suitable for attachment. Once the suture sleeve lumen 136 is positioned adjacent to tissue, sutures (not shown) may be tightly wrapped around the suture sleeve 108 in the suture grooves 134 and sutured to the patient's tissue. The tightly wrapped sutures in the suture grooves 134 can compress the inner surface 132 of the suture sleeve 108 adjacent to the suture grooves 134 against the lead body 120, securing the lead body 120 within the suture sleeve 108.

The suture sleeve 108 can be drug eluting, as describe below. It has been found that bacteria may migrate along the lead body 120. Bacteria growth can be particularly aggressive under the edge of the suture sleeve 108 in suture sleeve lumen 136. The antimicrobial drug eluting from suture sleeve 108 can kill bacteria along the lead body 120 and within the pocket adjacent to the suture sleeve 108 to reduce pocket infections, bacteremia, or endocarditis.

Figure 3:
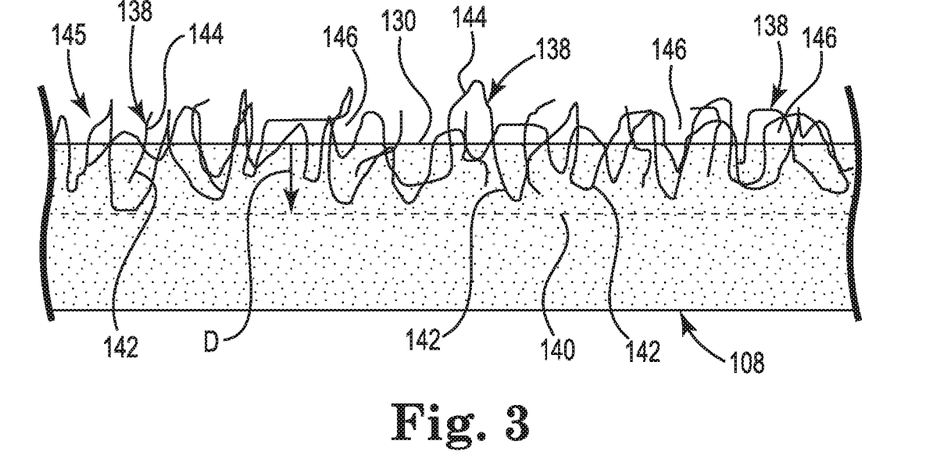
FIG. 3 is an enlarged schematic cross-sectional view of a portion of the suture sleeve of FIG. 2 illustrating the outer surface of the suture sleeve, according to some embodiments.

FIG. 3 is an enlarged schematic cross-sectional view of a portion of the suture sleeve 108 of FIG. 2 illustrating the outer surface 130 of the suture sleeve 108, according to some embodiments. As shown in FIG. 3, the suture sleeve 108 includes a first plurality of nanofibers 138 and a suture sleeve body 140. The suture sleeve body 140 can be formed of any suitable biostable, biocompatible polymer, such as a silicone or a polyurethane. Thus, the suture sleeve body 140 can be a polymer substrate. The suture sleeve body 140 can be formed by any suitable means including, for example, by molding. Each nanofiber of the first plurality of nanofibers 138 includes a first portion 142 and a second portion 144. Each nanofiber of the first plurality of nanofibers 138 can wind its way into and out of the suture sleeve body 140 to define the first portion 142 and the second portion 144. The first portion 142 is defined as those portions of the nanofiber that are embedded in, or interpenetrated with, at least a portion of the suture sleeve body 140 at the outer surface 130. The first portion 142 can extend from the outer surface 130 into the suture sleeve body 140 to a depth D. The first portion 142 is mechanically fixed to the substrate by virtue of the embedded, interpenetrating structure.

The second portion 144 is defined as those portions of the nanofiber that project from the outer surface 130. The projecting nanofibers of second portion 144 form a first plurality of interstitial spaces, or pores 146, between adjacent nanofibers or portions of nanofibers of the first plurality of nanofibers 138.

In some embodiments, the depth D to which the first portion 142 extends may be as small as about 10 microns, about 20 microns, or about 30 microns, or as great as about 50 microns, about 60 microns, or about 125 microns, or may extend an amount within any range defined between any pair of the foregoing values. In some embodiments, the depth D may range from about 10 microns to about 125 microns, about 20 microns to about 60 microns, or about 30 microns to about 50 microns. In some embodiments, the depth D may be about 40 microns.

In some embodiments, the first plurality of nanofibers 138 can have an average diameter as small as about 100 nanometers, about 200 nanometers, or about 400 nanometers, or as large as about 600 nanometers, about 800 nanometers, or about 1,000 nanometers, or have an average diameter between any of the preceding average diameters. In some embodiments, the average diameter of the first plurality of nanofibers 138 can range from about 100 nanometers to about 1,000 nanometers, about 200 nanometers to about 800 nanometers, or about 400 nanometers to about 600 nanometers. The average diameter may be determined by averaging measurements of the average diameter among the first plurality of nanofibers 138. The size of the first plurality of pores 146 may vary with the average diameter of the first plurality of nanofibers 138, with a larger average diameter resulting in a larger average size of the first plurality of pores 146.

In some embodiments, the first plurality of nanofibers 138 may include any suitable biocompatible polymer that can be formed into nanofibers. In some embodiments in which the first plurality of nanofibers 138 is biostable, the first plurality of nanofibers 138 can include a fluoropolymer, such as polytetrafluoroethylene (PTFE), polyvinlyidene fluoride (PVDF), or poly(vinylidene fluoride-co-hexafluoropropene) (PVDF-HPV); a polyurethane, such as polyether polyurethane, polycarbonate polyurethane, or polyisobutylene-polyurethane (PIB-PUR); or styrene-isobutylene-styrene (SIBS). In other embodiments in which the first plurality of nanofibers 138 is bioresorbable, the first plurality of nanofibers 138 can include poly(lactic-co-glycolic) acid (PLGA), polycaprolactone (PCL), poly-L-lactide (PLLA), or poly (lactide-co-glycolide)-block-poly(ethylene glycol). In some embodiments, the first plurality of nanofibers 138 can be formed by electro-spinning, as is known in the art.

In some embodiments, the first portion 142 of the first plurality of nanofibers 138 is interpenetrated with or embedded in the suture sleeve body 140 while the suture sleeve body 140 is in a liquid or semi-liquid state and the second portion 144 projects away from the outer surface 130. When the suture sleeve body 140 solidifies, the first portion 142 is embedded in the suture sleeve body 140 and the second portion 144 projects away from the outer surface 130. In some embodiments in which the suture sleeve body 140 is made of a thermoset polymer, such as a silicone, the first portion 142 of the first plurality of nanofibers 138 can be interpenetrated with the suture sleeve body 140 while the polymer is in a liquid or semi-liquid state before it is solidified by curing or cross-linking portions of the polymer around portions of the first portion 142. In other embodiments in which the suture sleeve body 140 is made of a thermoplastic polymer, the first plurality of nanofibers 138 can be interpenetrated with the suture sleeve body 140 while the polymer is in a liquid or semi-liquid state created by heating the polymer to melt or soften a portion of the suture sleeve body 140 at the outer surface 130, or by dissolution of the portion of the suture sleeve body 140 at the outer surface 130 in a suitable solvent. For example, if the suture sleeve body 140 is formed of a polyurethane, then tetrahydrofuran or dimethylformamide may be used to soften the suture sleeve body 140, creating a semi-liquid state. Once the first portion 142 of the first plurality of nanofibers 138 has interpenetrated the suture sleeve body 140, the suture sleeve body 140 can be cooled, or the solvent permitted to evaporate, to solidify the suture sleeve body 140, mechanically fixing the first portion 142 within the suture sleeve body 140.

In some embodiments, interpenetrating the first portion 142 of the first plurality of nanofibers 138 within the suture sleeve body 140 includes electro-spinning a nanofiber directly into the suture sleeve body 140 while the portion of the suture sleeve body 140 at the outer surface 130 is in a liquid or semi-liquid state.

In some embodiments, the at least one antimicrobial drug can be blended with a bioresorbable polymer, such as any mentioned above, and the first plurality of nanofibers 138 formed from this blend by electro-spinning, thus forming a drug eluting layer 145. In such embodiments, the antimicrobial drug is disposed within the first plurality of nanofibers 138. That is, the antimicrobial drug is integrated into the bioresorbable polymer itself such that as the bioresorbable polymer is broken down by the body, the antimicrobial drug is released from the first plurality of nanofibers 138. In this way, the antimicrobial drug and the plurality of nanofibers 138 can be configured to elute the antimicrobial drug from within the first plurality of nanofibers 138 as they are bioresorbed by the body. As used herein, a bioresorbable polymer is a polymer that may be broken down by biological systems to such an extent that it may be completely eliminated from the body. This is in contrast to a bioabsorbable polymer which is a polymer that may be broken down by biological systems, but not necessarily to the extent that it may be completely eliminated from the body.

Figure 4:
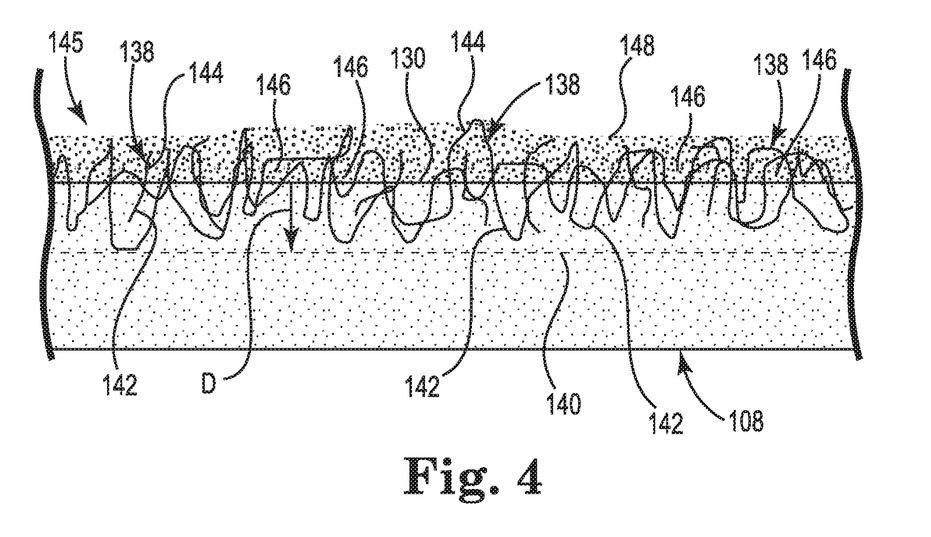
FIG. 4 is a schematic cross-sectional view of the portion of the suture sleeve of FIG. 3 illustrating a drug eluting layer on the outer surface of the suture sleeve, according to some embodiments.

FIG. 4 is a schematic cross-sectional view of the portion of the suture sleeve 108 of FIG. 3 illustrating another embodiment of the drug eluting layer 145 on the outer surface 130 of the suture sleeve 108. As shown in the embodiment of FIG. 4, the suture sleeve 108 can further includes an antimicrobial drug component 148 disposed within at least some of the first plurality or pores 146, thus forming the drug eluting layer 145. In some embodiments, the antimicrobial drug component 148 can consist of one or more antimicrobial drugs contained in the first plurality of pores 146. The rate of elution of the one or more antimicrobial drugs can be controlled by the size of the first plurality of pores 146, with smaller pores resulting in a lower elution rate. In some embodiments, the antimicrobial drug component 148 can include a colloid suspension of the one or more antimicrobial drugs. In some embodiments, the colloid suspension may be stabilized by addition of poly (ethylene glycol).

In some other embodiments, the antimicrobial drug component 148 further includes a suitable hydrophilic polymer, such as poly(ethylene glycol), that has been blended with the least one antimicrobial drug. After being disposed within the pores 146 by, for example, diffusion or absorption, and then cross-linked around and between at least some of the second portion 144 to mechanically fix the antimicrobial drug component 148 to the first plurality of nanofibers 138. In this way, the at least one antimicrobial drug and the plurality of nanofibers 138 can be configured to elute the antimicrobial drug from among the first plurality of nanofibers 138.

In some embodiments, the poly(ethylene glycol) can include a radical initiator compound that generates free radicals when exposed to energy, such as ultraviolet radiation or heat. The free radicals can initiate cross-linking of the poly(ethylene glycol). Examples of suitable UV initiator compounds include (4-bromophenyl)diphenylsulfonium triflate, (4-fluorophenyl)diphenylsulfonium triflate, (4-iodophenyl)diphenylsulfonium triflate, (4-methoxyphenyl)diphenylsulfonium triflate, (4-methylphenyl) diphenylsulfonium triflate, (4-methylthiophenyl)methyl phenyl sulfonium triflate, (4-phenoxyphenyl)diphenylsulfonium triflate, (4-phenylthiophenyl)diphenylsulfonium triflate, (4-tert-butylphenyl)diphenylsulfonium triflate, (cumene)cyclopentadienyliron(II) hexafluorophosphate, (tert-butoxycarbonylmethoxynaphthyl)-diphenylsulfonium triflate, 1-naphthyl diphenylsulfonium triflate, 2-(4-methoxystyryl)-4,6-bis(trichloromethyl)-1,3,5-triazine, bis(4-tert-butylphenyl)iodonium perfluoro-1-butanesulfonate bis(4-tert-butylphenyl)iodonium p-toluenesulfonate, bis(4-tert-butylphenyl)iodonium triflate, boc-methoxyphenyldiphenylsulfonium triflate, diphenyliodonium hexafluorophosphate, diphenyliodonium nitrate, diphenyliodonium perfluoro-1-butanesulfonate, diphenyliodonium p-toluenesulfonate, diphenyliodonium triflate, N-hydroxy-5-norbornene-2,3-dicarboximide perfluoro-1-butanesulfonate, N-hydroxynaphthalim ide triflate, triarylsulfonium hexafluoroantimonate salts, triphenylsulfonium perfluoro-1-butanesufonate, triphenylsulfonium triflate, tris(4-tert-butylphenyl)sulfonium perfluoro-1-butanesulfonate, and tris(4-tert-butylphenyl)sulfonium triflate. Examples of suitable thermal initiator compounds include azobisisobutyronitrile (AIBN), dibenzoyl peroxide, N-benzyl pyridinium bromide, N-benzyl o-cyano pyridinium bromide, N-benzyl p-cyanopyridinium bromide, N-benzyl N, N-dimethyl anilinium bromide, and benzyl triphenyl phosphonium bromide.

Thus, in some embodiments, the cross-linked poly(ethylene glycol) of the antimicrobial drug component 148 can include a residue of a cross-linking initiator. For example, the initiator residue may include, for example, a residue of any of the ultraviolet initiators or the thermal initiators describe above.

In the embodiment of FIG. 4, the second portion 144 of the first plurality of nanofibers 138 can be formed as described above in reference to FIG. 3, and coated with the antimicrobial drug component 148 so that it can be disposed into the first plurality of pores 146. In some embodiments, coating the second portion 144 with the antimicrobial drug component 148 can included dipping the outer surface 130 into the at least one antimicrobial drug or the blend of the at least one antimicrobial drug and the poly(ethylene glycol) in a liquid state. In other embodiments, coating the second portion 144 with the antimicrobial drug component 148 can include spraying the at least one antimicrobial drug or the blend of the at least one antimicrobial drug and the poly(ethylene glycol) in a liquid state onto the outer surface 130.

In some embodiments, the cross-linked poly(ethylene glycol) of the antimicrobial drug component 148 can be covalently bonded to the second portion 144 of the first plurality of nanofibers 138, in addition to being mechanically fixed to the second portion 144. In such embodiments, the cross-linked poly(ethylene glycol) is both chemically and mechanically fixed to the second portion 144. In such embodiments, incorporating the antimicrobial drug component 148 into the first plurality of pores 146 can include exposing the second portion 144 and the antimicrobial drug component 148 including the poly(ethylene glycol) and the at least one antimicrobial drug to a plasma that contains argon. Free radicals formed by the argon-containing plasma produce reactive sites for covalent bonding of the poly(ethylene glycol) to the second portion 144 of the first plurality of nanofibers 138. The argon-containing plasma does not include oxygen, as the oxygen has been found to deteriorate the first plurality of nanofibers 138. In some embodiments, the argon-containing plasma can produced from a flow of argon gas at a pressure of about 250 mTorr and an applied radio-frequency power of about 200 Watts. The second portion 144 and the first plurality of nanofibers 138 can be exposed to the plasma for a time ranging from about 60 seconds to about 180 seconds.

In some embodiments, the free radicals generated by exposure to the argon-containing plasma not only provide reactive sites for covalent bonding of the poly(ethylene glycol) to the second portion 144, but may also provide free radicals for the cross-linking of the poly(ethylene glycol). In such embodiments, there may be no need for an ultraviolet initiator or a thermal initiator, and no initiator residues present in the cross-linked poly(ethylene glycol) portion of the antimicrobial drug component 148.

Figure 5:
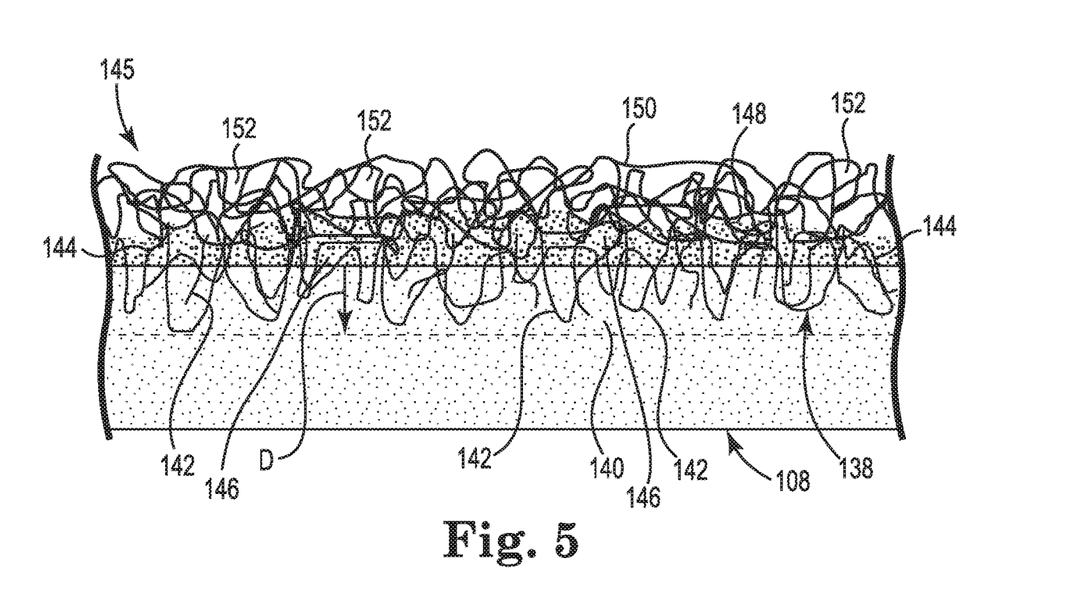
FIG. 5 is a schematic cross-sectional view of the portion of the suture sleeve of FIG. 4 illustrating a drug eluting layer on the outer surface of the suture sleeve, according to some embodiments.

FIG. 5 is a schematic cross-sectional view of the portion of the suture sleeve 108 of FIG. 4 illustrating another embodiment of the drug eluting layer 145 on the outer surface 130 of the suture sleeve 108. As shown in the embodiment of FIG. 5, in some embodiments, the suture sleeve 108 can further include a second plurality of nanofibers 150 disposed on the first plurality of nanofibers 138. The second plurality of nanofibers 150 may be formed by electro-spinning, as with the first plurality of nanofibers 138, forming a second plurality of interstitial spaces, or pores 152, between adjacent nanofibers 150. The second plurality of nanofibers 150 with pores 152 can limit the rate of elution of the one or more antimicrobial drugs from the antimicrobial drug component 148 by providing a barrier through which the antimicrobial drugs must diffuse.

In some embodiments, the second plurality of nanofibers 150 can be formed on the first plurality of nanofibers 138 by electro-spinning. In some embodiments, the second plurality of nanofibers 150 can be electro-spun onto the first plurality of nanofibers 138 before incorporating the antimicrobial drug component 148 within the first plurality of pores 146, as described above in reference to FIG. 4. In some other embodiments, the second plurality of nanofibers 150 can be electro-spun onto the first plurality of nanofibers 138 after incorporating the antimicrobial drug component 148 within the first plurality of pores 146, as described above in reference to FIG. 4.

In some embodiments, the second plurality of nanofibers 150 can be partially interwoven with the first plurality of nanofibers 138 as a result of electro-spinning the second plurality of nanofibers 150 directly onto the first plurality of nanofibers 138. In some embodiments, the second plurality of nanofibers 150 can be thermally bonded to the first plurality of nanofibers 138.

In some embodiments, the second plurality of nanofibers 150 may include any suitable biocompatible polymer that can be formed into nanofibers. In some embodiments in which the second plurality of nanofibers 150 is biostable, the second plurality of nanofibers 150 can include a fluoropolymer, such as polytetrafluoroethylene (PTFE), polyvinylidene fluoride (PVDF), or poly(vinylidene fluoride-co-hexafluoropropene) (PVDF-HPV); a polyurethane, such as polyether polyurethane, polycarbonate polyurethane, or polyisobutylene-polyurethane (PIB-PUR); or styrene-isobutylene-styrene (SIBS). In some embodiments, the second plurality of nanofibers 150 can be formed by electro-spinning, as is known in the art.

In some embodiments, the second plurality of nanofibers 150 can have an average diameter as small as about 100 nanometers, about 200 nanometers, or about 400 nanometers, or as large as about 600 nanometers, about 800 nanometers, or about 1,000 nanometers, or have an average diameter between any of the preceding average diameters. In some embodiments, the average diameter of second plurality of nanofibers 150 can range from about 100 nanometers to about 1,000 nanometers, about 200 nanometers to about 800 nanometers, or about 400 nanometers to about 600 nanometers. The average diameter may be determined by averaging measurements of the average diameter among the second plurality of nanofibers 150. The size of the second plurality of pores 152 may vary with the average diameter of the second plurality of nanofibers 150, with a larger average diameter resulting in a larger average size of the second plurality of pores 152. In some embodiments, the size of the second plurality of pores 152 can be smaller than the size of the first plurality of pores 146 to further limit the rate of elution of the one or more antimicrobial drugs from the antimicrobial drug component 148.

Figure 6:
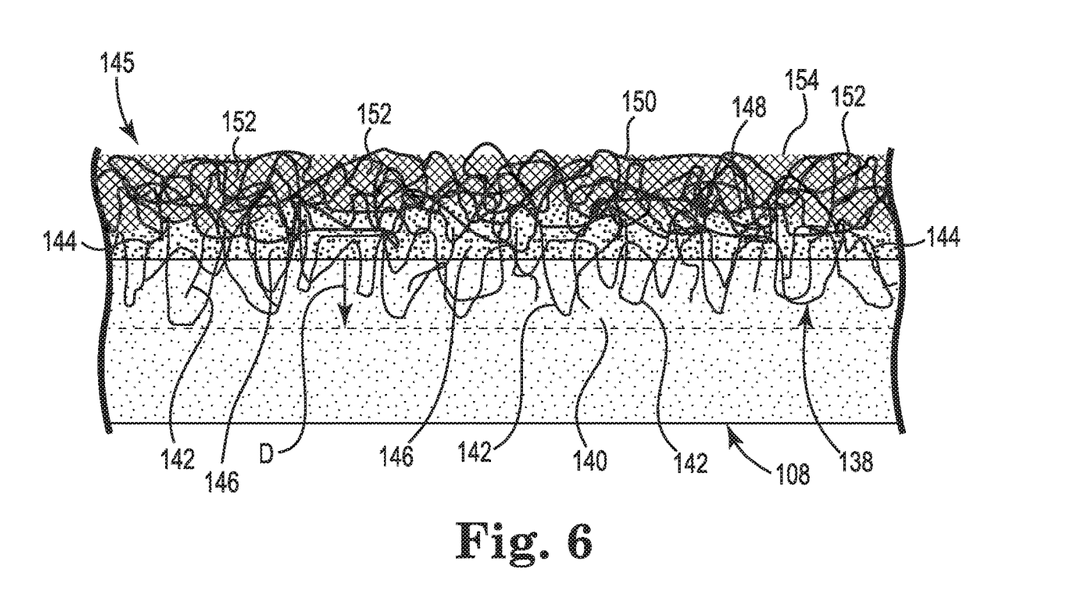
FIG. 6 is a schematic cross-sectional view of the portion of the suture sleeve of FIG. 5 illustrating another embodiment of a drug eluting layer on the outer surface of the suture sleeve.

FIG. 6 is a schematic cross-sectional view of the portion of the suture sleeve 108 of FIG. 5 illustrating another embodiment of the drug eluting layer 145 on the outer surface 130 of the suture sleeve 108. As shown in the embodiment of FIG. 6, the suture sleeve 108 can further includes an antimicrobial drug component 154 disposed within at least some of the second plurality of pores 152. The antimicrobial drug component 154 can be as described above for any of the embodiments of the antimicrobial drug component 148. The rate of elution of the one or more antimicrobial drugs can be controlled by the size of the second plurality of pores 152, with smaller pores resulting in a lower elution rate.

In some embodiments, the antimicrobial drug component 154 can be identical to the antimicrobial drug component 148. In other embodiments, the antimicrobial drug component 154 can be different from the antimicrobial drug component 148. For example, in some embodiments, the antimicrobial drug component 154 may be configured to elute over a shorter period of time to provide a strong, initial dose against any bacteria on the suture sleeve 108 at the time of implantation, while the antimicrobial drug component 148 may be configured to elute over a longer period of time to provide on-going antimicrobial protection within the subcutaneous pocket. In some embodiments, the period of time for the antimicrobial drug component 154 to elute can be up to 2 hours, up to 4 hours, or up to 6 hours or up to any time between any to the preceding times. In some embodiments, the period of time for the antimicrobial drug component 148 to elute can be up to 6 hours, up to 10 hours, up to 24 hours, up to 2 days, up to 4 days, up to 6 days, up to 1 week, up to 2 weeks, up to 3 weeks, up to 4 weeks, up to 2 months, up to 4 months, or up to 6 months, or up to any period of time between any two of the preceding times.

Figure 7:
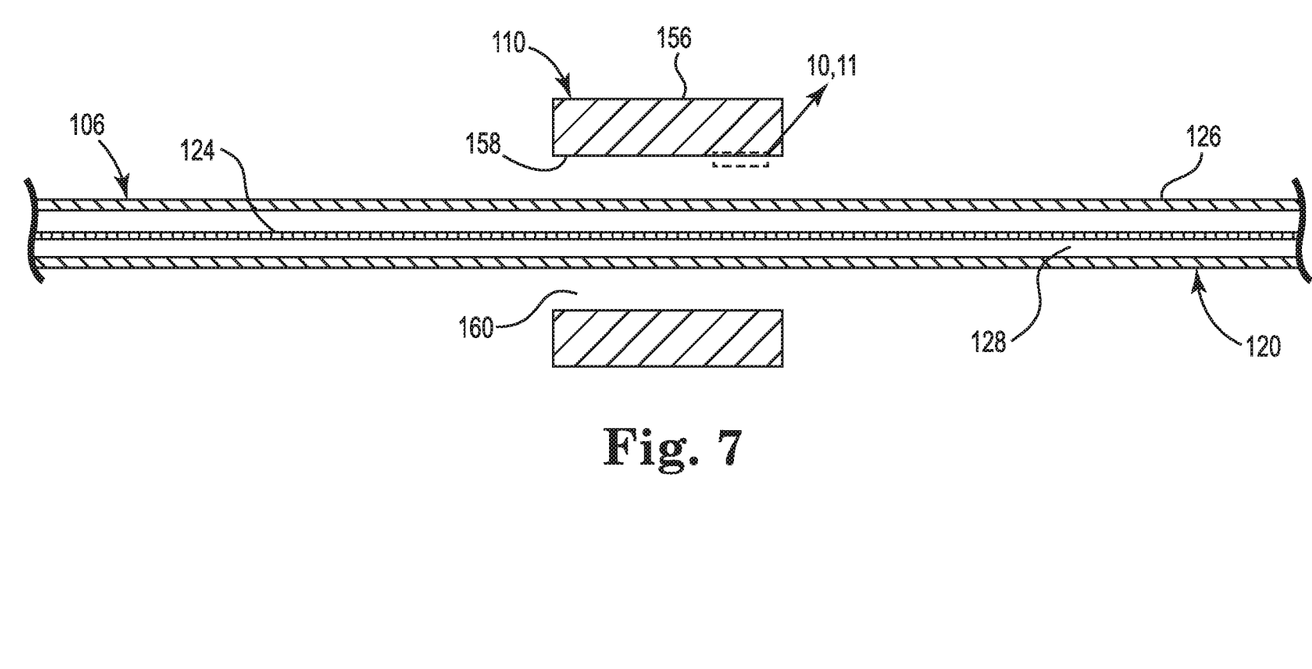
FIG. 7 is a schematic cross-sectional view of a portion of the implantable medical electrical lead of FIG. 1 showing a ring about the lead body.

FIGS. 7-11 describe a drug eluting layer on an inner surface of the ring 110, according to some other embodiments. FIG. 7 is a schematic cross-sectional view of a portion of the implantable medical electrical lead 106 of FIG. 1 showing the ring 110 about the lead body 120. As shown in the embodiment of FIG. 7, the ring 110 includes an outer surface 156 and an inner surface 158. The inner surface 158 defines a ring lumen 160 extending the length of the ring 110. A diameter of the ring lumen 160 is greater than a diameter of the lead body 120 such that the ring lumen 160 may be moved along the lead body 120 to a suitable location within the subcutaneous pocket.

The ring 110 can be drug eluting, as describe below. It has been found that bacteria may migrate along the lead body 120. As with the suture sleeve 108 described above, the antimicrobial drug eluting from ring 110 can kill bacteria along the lead body 120 and within the pocket to reduce pocket infections, bacteremia, or endocarditis.

Figure 8:
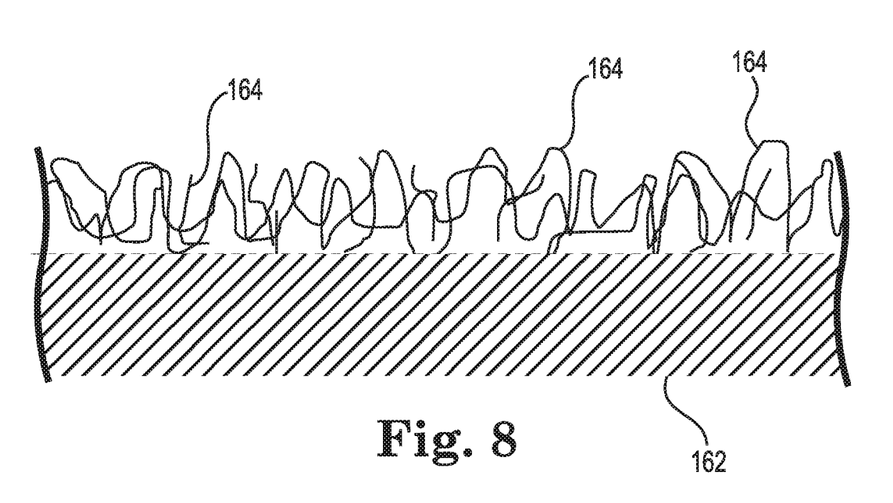
FIGS. 8, 9, and 10 are enlarged schematic cross-sectional views of a portion of the ring of FIG. 7 illustrating the formation of a drug eluting layer on an inner surface of the ring, according to some embodiments.
Figure 9:
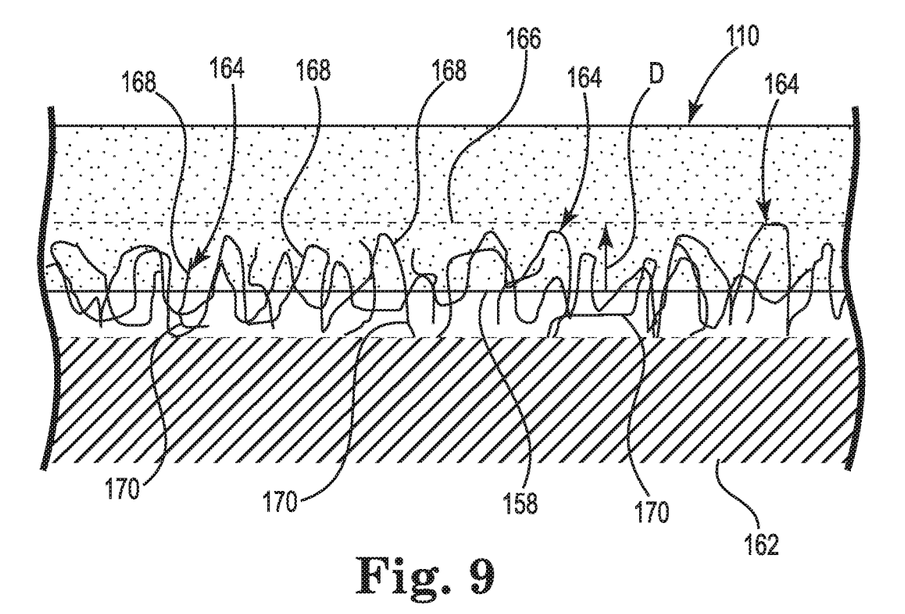
Figure 10:
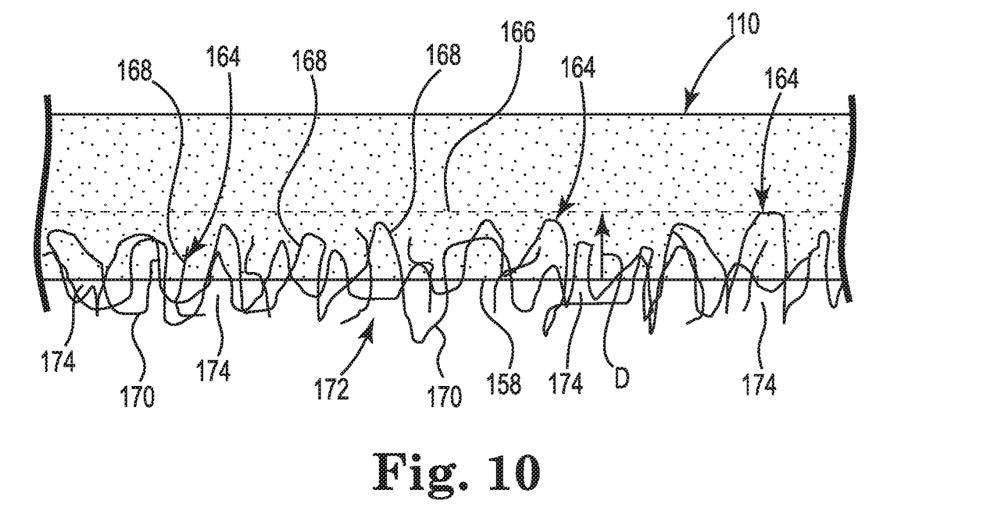

FIGS. 8-10 are enlarged schematic cross-sectional views illustrating the formation of a drug eluting layer on the inner surface 158 of the ring 110, according to some embodiments. FIG. 8 shows a core pin or mandrel 162 and a plurality of nanofibers 164 disposed onto the core pin or mandrel 162. The plurality of nanofibers 164 can be similar or identical to the first plurality of nanofibers 138 described above in reference to FIGS. 3 and 4. The plurality of nanofibers 164 can be electro-spun onto the core pin or mandrel 162. The core pin or mandrel 162 can be rotated while the plurality of nanofibers 164 is electro-spun onto the core pin or mandrel 162.

After the plurality of nanofibers 164 is formed onto the core pin or mandrel 162, the plurality of nanofibers 164 and the core pin or mandrel 162 can be over-molded with a ring body 166 to form the ring 110 with the inner surface 158, as shown in FIG. 9. The ring body 166 can be formed of any suitable biostable, biocompatible polymer, such as a silicone or a polyurethane. Thus, the ring body 166 can be a polymer substrate. For example, the body 166 can be made of silicone, in which case liquid silicone rubber is injected into a mold (not shown) containing the core pin or mandrel 162 and the plurality of nanofibers 164. The liquid silicone rubber does not fully penetrate through the plurality of nanofibers 164 to the core pin or mandrel 162 because of its relatively high viscosity and the relatively small size of the spaces formed among the plurality of nanofibers 164 as it is electro spun onto the core pin or mandrel 162. Thus, the inner surface 158 is spaced apart from the core pin or mandrel 162.

Each nanofiber of the plurality of nanofibers 164 includes a first portion 168 and a second portion 170. Each nanofiber of the plurality of nanofibers 164 can wind its way into and out of the ring body 166 to define the first portion 168 and the second portion 170. The first portion 168 is defined as those portions of the nanofiber that are embedded in, or interpenetrated with, at least a portion of the ring body 166 at the inner surface 158. The first portion 168 can extend from the inner surface 158 into the ring body 166 to a depth D. The first portion 168 is mechanically fixed to the substrate by virtue of the embedded, interpenetrating structure.

The second portion 170 is defined as those portions of the nanofiber that project from the inner surface 158. The projecting nanofibers of second portion 170 form a plurality of interstitial spaces, or pores 174, between adjacent nanofibers or portions of nanofibers of the plurality of nanofibers 164.

After the silicone cross-links or cures, the core pin or mandrel 162 can be removed, as shown in FIG. 10, forming a drug eluting layer 172 on the inner surface 158 of the ring 110 similar to the embodiments described above in reference to FIG. 3 on the outer surface 130 of the suture sleeve 108.

Figure 11:
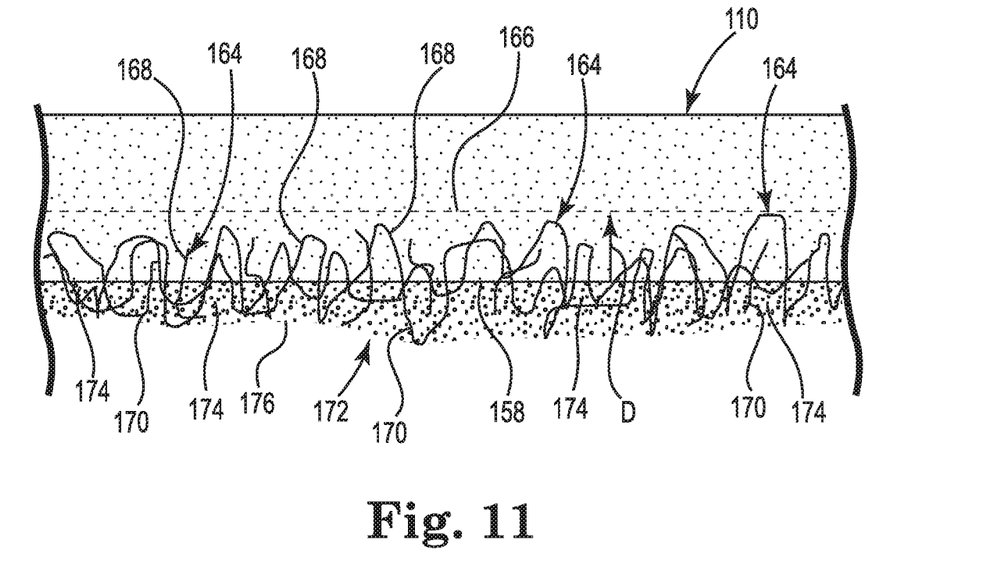
FIG. 11 is a schematic cross-sectional view of the portion of the ring 110 of FIG. 7 illustrating another embodiment of a drug eluting layer on the inner surface of the ring.

FIG. 11 is a schematic cross-sectional view of the portion of the ring 110 of FIG. 7 illustrating another embodiment of the drug eluting layer 172 on the inner surface 158 of the ring 110. As shown in the embodiment of FIG. 11, the ring 110 can further include an antimicrobial drug component 176 disposed within at least some of the plurality of pores 174, thus forming the drug eluting layer 172. The antimicrobial drug component 176 can the same as any of the embodiments of the antimicrobial drug component 148 described above in reference to FIG. 4.

Although the embodiments described above in reference to FIGS. 7-11 are directed to the drug eluting layer 172 formed on the inner surface 158 of the ring 110, it is understood that these embodiments may also be applied to the inner surface 132 of the suture sleeve 108. Similarly, although the embodiments described above in reference to FIGS. 3-6 are directed to the drug eluting layer 145 formed on the outer surface 130 of the suture sleeve 108, it is understood that these embodiments may also be applied to the outer surface 156 of the ring 110.

Although poly(ethylene glycol) is described as the hydrophilic polymer in the above embodiments, other suitable hydrophilic polymers can include polyvinylpyrrolidone (PVP), poly(2-methyl-2-oxazoline), poly(2-ethyl-2-oxazoline, poly(ethylene glycol) methacrylate, and hydroxypropyl cellulose. In some embodiments, the hydrophilic polymer may be a hydroxy-terminated polymer, such as poly(ethylene glycol). In other embodiments, the hydrophilic polymer may be terminated by a different functional group that may aid in cross-linking. For example, the poly(ethylene glycol) can be terminated with a methacrylate group.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable drug eluting medical device comprising:
   a polymer substrate having a surface;
   a first plurality of nanofibers, each nanofiber of the first plurality of nanofibers including:
      a first portion interpenetrated with the surface of the substrate to mechanically fix the nanofiber to the substrate; and
      a second portion projecting from the surface, the second portion of the first plurality of nanofibers forming a first plurality of pores;
   a second plurality of nanofibers disposed on the first plurality of nanofibers, the second plurality of nanofibers forming a second plurality of pores; and
   at least one antimicrobial drug disposed within at least some of the first plurality of pores to elute from the device.

2. The implantable medical device of claim 1, wherein the first plurality of nanofibers is formed of a bioresorbable polymer.

3. The implantable medical device of claim 1, further including cross-linked poly(ethylene glycol) containing the at least one antimicrobial drug, the cross-linked poly(ethylene glycol) containing the at least one antimicrobial drug disposed within the first plurality of pores and mechanically fixed to the second portion of the first plurality of nanofibers.

4. The implantable medical device of claim 3, wherein the cross-linked poly(ethylene glycol) containing the at least one antimicrobial drug is bonded to the second portion of the first plurality of nanofibers by covalent bonds.

5. The implantable medical device of claim 1, wherein the second plurality of nanofibers are thermally bonded to the first plurality of nanofibers.

6. The implantable medical device of claim 1, wherein the second plurality of pores has an average pore size that is smaller than an average pore size of the first plurality of pores.

7. The implantable medical device of claim 1, further comprising a second at least one antimicrobial drug disposed among the second plurality of nanofibers, wherein the second at least one antimicrobial drug can be the same or different than the at least one antimicrobial drug disposed within or among the second portion of the first plurality of nanofibers.

8. The implantable medical device of claim 1, wherein first plurality of nanofibers has an average diameter ranging from about 100 nanometers to about 1,000 nanometers.

* * * * *